(12) United States Patent
Yun et al.

(10) Patent No.: US 8,068,579 B1
(45) Date of Patent: Nov. 29, 2011

(54) PROCESS FOR EXAMINING MINERAL SAMPLES WITH X-RAY MICROSCOPE AND PROJECTION SYSTEMS

(75) Inventors: Wenbing Yun, Walnut Creek, CA (US); Michael Feser, Walnut Creek, CA (US); Andrei Tkachuk, Walnut Creek, CA (US); Thomas A. Case, Walnut Creek, CA (US); Frederick W. Duewer, Albany, CA (US); Hauyee Chang, Berkeley, CA (US)

(73) Assignee: Xradia, Inc., Pleasanton, CA (US)

( * ) Notice: Subject to any disclaimer, the term of this patent is extended or adjusted under 35 U.S.C. 154(b) by 0 days.

(21) Appl. No.: 12/421,380

(22) Filed: Apr. 9, 2009

Related U.S. Application Data

(60) Provisional application No. 61/043,437, filed on Apr. 9, 2008.

(51) Int. Cl.
*G01N 23/00* (2006.01)
(52) U.S. Cl. .............................................. 378/21; 378/4
(58) Field of Classification Search ............... 378/43, 378/21–27, 41, 4
See application file for complete search history.

(56) References Cited

U.S. PATENT DOCUMENTS

| | | | | |
|---|---|---|---|---|
| 5,627,874 A * | 5/1997 | Smallbone | ..................... | 378/208 |
| 6,052,431 A * | 4/2000 | Onoguchi et al. | ............... | 378/84 |
| 6,655,192 B2 * | 12/2003 | Chavdar | ............................ | 73/38 |
| 7,215,736 B1 * | 5/2007 | Wang et al. | ..................... | 378/25 |
| 2008/0165924 A1 * | 7/2008 | Wang et al. | ..................... | 378/27 |

* cited by examiner

*Primary Examiner* — Hoon Song
(74) *Attorney, Agent, or Firm* — Houston Eliseeva LLP

(57) ABSTRACT

A process to determine the porosity and/or mineral content of mineral samples with an x-ray CT system is described. Based on the direct-projection techniques that use a spatially-resolved x-ray detector to record the x-ray radiation passing through the sample, 1 micrometer or better resolution is achievable. Furthermore, by using an x-ray objective lens to magnify the x-ray image in a microscope configuration, a higher resolution of up to 50 nanometers or more is achieved with state-of-the-art technology. These x-ray CT techniques directly obtain the 3D structure of the sample with no modifications to the sample being necessary. Furthermore, fluid or gas flow experiments can often be conducted during data acquisition so that one may perform live monitoring of the physical process in 3D.

29 Claims, 2 Drawing Sheets

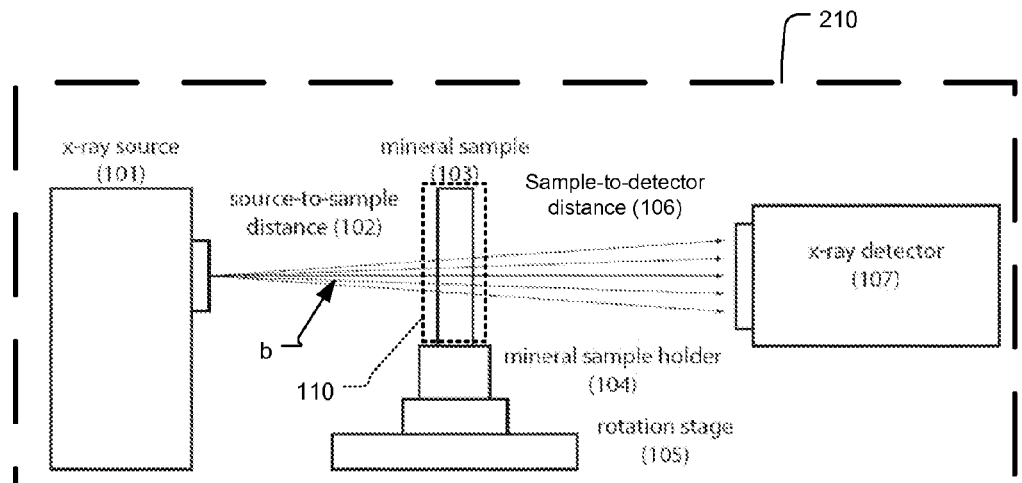
Fig. 1
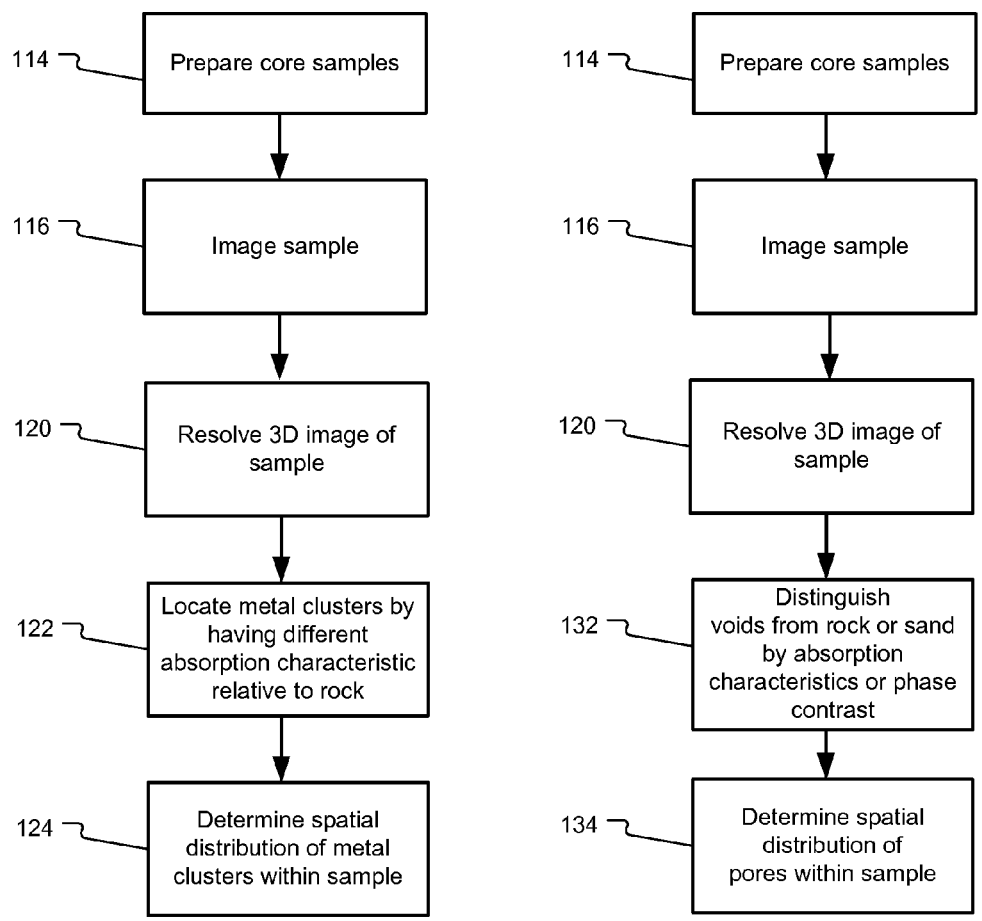
Fig. 2
Fig. 3

PROCESS FOR EXAMINING MINERAL SAMPLES WITH X-RAY MICROSCOPE AND PROJECTION SYSTEMS

RELATED APPLICATIONS

This application claims the benefit under 35 USC 119(e) of U.S. Provisional Application No. 61/043,437, filed on Apr. 9, 2008, which is incorporated herein by reference in its entirety.

BACKGROUND OF THE INVENTION

X-ray imaging, including projection and microscopy techniques, have been widely used in medical imaging and industrial inspection since their invention. A particularly important development is the computed tomography (CT) techniques that allow the three dimensional (3D) structure of a sample to be reconstructed from a series of two dimensional (2D) x-ray images acquired at different view angles. Furthermore, recent advances in micro x-ray CT has pushed the 3D resolution to 1 micrometer with direct-projection type imaging systems, while using x-ray objective lenses, such as Fresnel zone plates, 3D images with up to 50 nanometer resolution have been demonstrated.

Mineral samples analysis for mining is important as ores are used in metal production and crude oil extracted from bituminous sand and coal provide a substantial proportion of our energy consumption. Understanding the structure of the mineral samples is therefore important for using them effectively and locating mining operations. This often involves examining the porous structures in the sample. Traditionally, this is usually accomplished with indirect measurements such as running fluid through the sample and measuring the flow rate under different pressures. Any imaging techniques are often destructive involving lapping and polishing the sample and then imaging with light microscope or scanning electron microscope.

SUMMARY OF THE INVENTION

The existing mineral imaging techniques are typically inaccurate and prone to introducing artifacts. On the other hand, x-ray CT has nanometer to micrometer resolution, provides a non-destructive means to obtain the exact 3D structure of these samples, and furthermore fluid or gas flow experiments can often be conducted during data acquisition so that one may perform live monitoring of the physical process in 3D.

This invention concerns a process to determine the porosity and/or mineral content of mineral samples with an x-ray CT system. Based on the direct-projection techniques that use a spatially-resolved x-ray detector to record the x-ray radiation passing through the sample, 1 micrometer or better resolution is achievable. Furthermore, by using an x-ray objective lens to magnify the x-ray image in a microscope configuration, a higher resolution of up to 50 nanometers or more is achieved with state-of-the-art technology. These x-ray CT techniques directly obtain the 3D structure of the sample with no modifications to the sample being necessary. Furthermore, fluid or gas flow experiments can often be conducted during data acquisition so that one may perform live monitoring of the physical process in 3D.

In general, according to one aspect, the invention features a process of determining the porosity and/or internal composition inside a mineral sample with an x-ray imaging system. The process comprises extracting small core samples from different regions of the mineral sample, possibly shaping the core samples into small cylindrical or rectangular pillar shapes, placing the core samples into an x-ray imaging system with magnification between 2× and 5,000×, acquiring magnified radiographs from x-rays transmitted through the core samples at different view angles, and reconstructing a 3D image with computer tomography algorithms.

In preferred embodiment, the core samples are shaped into cylindrical shapes with diameter of 10-1,000 micrometers or pillar shapes with width of 10-1,000 micrometers with mechanical grinding and polishing or with lasers.

The x-ray imaging system preferably comprises a laboratory-based x-ray source, a condenser lens, a sample holder with a rotation stage, an objective lens, and a spatially resolved detector system. Options for the source include rotating anode x-ray sources and micro-focus x-ray sources. In a current embodiment, the condenser lens is an ellipsoid shaped capillary lens and the objective lens is a Fresnel zone plate lens, with the detector comprising a scintillator, a CCD camera, and a lens to image visible light image from the scintillator to the CCD camera.

In one embodiment, the process and x-ray system are used at the mining site with the x-ray imaging system being placed on a mobile platform mounted inside a motorized vehicle and with power supplied from the vehicle.

The x-ray system can rely on absorption contrast mode that records magnified x-ray shadow radiography or a phase contrast mode.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 1 shows a schematic illustration of the direct projection x-ray CT imaging system;

FIG. 2 is a flow diagram illustrating a process for analyzing a sample according to one embodiment;

FIG. 3 is a flow diagram illustrating a process for analyzing a sample for porosity according to another embodiment.

DETAILED DESCRIPTION OF THE PREFERRED EMBODIMENTS

Figure 4:
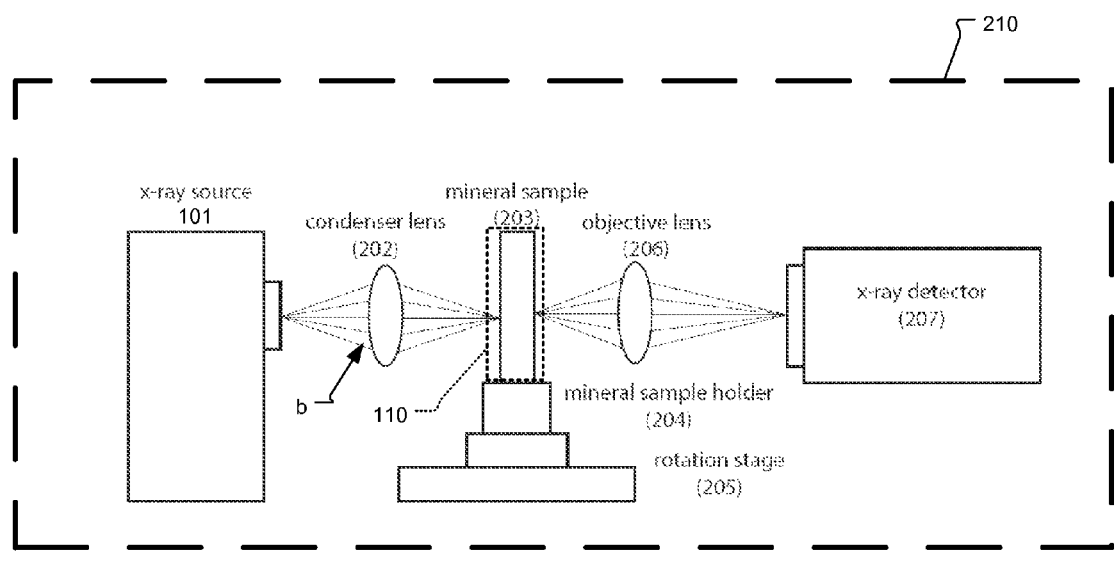
FIG. 4 shows a schematic illustration of the x-ray CT system that uses an x-ray lens to magnify the image in a microscope configuration of the imaging system.

This disclosure describes a process that uses an x-ray CT system to determine the porosity and/or mineral content of mineral samples. Examples samples include mineral samples such as sandstone, bituminous sand, ore samples, and coal or samples containing precious metals or fluids, such as water or crude oil.

A basic implementation is shown in FIG. 1. In this configuration, an x-ray source 101 generates x-ray radiation beam b. A mineral sample 103 is placed in the beam path b and the x-ray radiation passing through the sample 103 is recorded by a spatially resolved detector 107, having 1,024× 1,024 pixels, for example. The sample is mounted on sample holder 104 with an integrated rotation stage 105 that rotates the sample through a range of −90 degrees and +90 degrees from the optical axis.

With mineral samples, a high-energy x-ray radiation beam is used with an energy above several keV. This is typically required to penetrate sample with tens of micrometers or greater thickness. Higher energy radiation of tens of keV is used when the sample 103 is usually about a millimeter or greater in thickness. Generally the range is 5-150 keV.

The x-ray source 101 used in this configuration is preferably a laboratory based source such as sealed tube, rotating-anode, or micro-focus x-ray source. The target material is preferably Cu, W, Mo, Ag, or Rh. A synchrotron radiation x-ray source can alternatively be used. In this case, the source 101 also provides tunable energy that allows elemental-specific imaging of different compositions in the sample 103. The rotation stage 105 is preferably a mechanical ball-bearing or roller bearing stage. Air bearing stages are used to reduce rotation error in other embodiments.

In the configuration shown in FIG. 1 the magnification is determined by the source-to-sample distance 102 and sample-to-detector distance 106. With detectors that have coarse resolution, a small x-ray source spot size and high magnification is required to achieve high resolution. This means the sample-to-detector distance 106 will be much greater than the source-to-sample distance 102. This is typically accomplished by placing the sample 103 very close to the source 101. On the other hand, with high-resolution detector, the magnification can be relatively low, and the distances between the source, sample, and detector can be relaxed. Preferably the magnification is between 2×-100× for this projection system configuration.

The system shown in FIG. 1 can be used to examine a wide range of mineral samples. In one process, shown in FIG. 2, small core samples are extracted from the mining sample, typically with mechanical drills in step 114. The number of core samples is determined by the composition of the sample; for example, a core sample can be extracted from each representative region of the sample. The core samples are then shaped into small cylindrical or pillar shapes. This can be done by mechanical grinding and polishing or laser ablation techniques, or a combination of these techniques. The size of the cylinder or pillar depends on the x-ray energy. Preferably the cylindrical shapes have a diameter of 10-1,000 micrometers. Typically the diameter or the width is set to the 1/e attenuation length of the principle x-ray energy in use.

After each sample is shaped into the desired size, it is imaged in the x-ray imaging system of FIG. 1 or FIG. 4 in step 116. The imaging system generally records the radiograph of each sample, which is magnified geometrically or by an x-ray lens as described later. To obtain the 3D structure of the sample, multiple projections images are obtained at different view angles. A data set with 180-degree range is typically used to obtain a full range of projection data. A step size of 0.25 degree is typically used for radiographs with 1,024×1,024 pixels. Larger radiographs will require proportionally finer angular steps. Usually, the step size is 0.25 to 1 degree steps.

Upon completion, the projection data sets are reconstructed to obtain the 3D structure of each sample using tomographic reconstruction algorithms in step 120. Typical algorithms include filtered back-projection, algebraic reconstruction technique (ART) and its variants, and iterative statistical methods such as Baysian techniques.

The 3D data sets are analyzed to obtain the physical characteristics of each sample and thus the larger original mining sample. Pores are identified as low-absorption regions in the sample and porosity can be measured by computing the statistical properties of the pores in the sample.

Different mineral compositions can be determined by measuring the absorption properties at different volumes. For example precious metals such as gold will exhibit much higher attenuation than surrounding rock structures. Mineral content and distribution of the sample can be analyzed and measured quantitatively with this technique.

In more detail, metal clusters are distinguished from the rock by the absorption contrast characteristics in the CT image in step 122. The spatial distribution of the metal content is measured in 3D with the CT techniques in step 124.

In other processes, mineral samples important for oil exploration and extraction, such as sandstone or bituminous sand (tar sand), are examined with the systems shown in FIG. 1 or FIG. 4 to measure the porous structures and therefore understand fluid flow properties inside these type of sample. This process is shown in FIG. 3. In more detail, the sample is prepared in steps 114 and 116 as described above. Then sandstone or tar is examined to measure porosity by acquiring x-ray images at different angles and the 3D image computed using CT in step 120. Voids are distinguished from the rock or sand by the absorption characteristics or phase contrast in the CT image in step 132. The spatial distribution of the pores are measured in 3D with the CT techniques in step 134 and the porosity determined.

Coal samples can also be examined to measure its porous structures and potential efficiency and pollution content for energy generation.

An alternative configuration that is used with the methods of FIGS. 2 and 3 is shown in FIG. 4. This configuration increases the resolution of the instrumentation. An x-ray lens 206 is used to magnify the x-ray image of sample 203, which is held on a sample holder 204 with an integrated rotation stage 205 that rotates the sample through a range of −90 degrees and +90 degrees from the optical axis. The magnified image is then projected onto the spatially resolved detector system 207. Preferably the detector system comprises a scintillator, a CCD camera (having 1,024×1,024 pixels, for example), and a lens to image visible light from the scintillator onto the CCD camera. The x-ray lens is preferably Fresnel zone plate lens or compound refractive lens fabricated from Be, Al, or Si, etc. This configuration typically requires a condenser lens 202 to project the x-ray beam from source 101 to the sample 203. The condenser lens 202 is preferably a Fresnel zone plate lens, ellipsoidal reflective capillary lens, Wolter mirror lens, or compound refractive lens.

In one modification, a phase-ring is added to the optical train and the system operates in the phase contrast mode in addition to absorption contrast.

With the use of x-ray lenses, a higher magnification is achieved without excessive compromise on the throughput. The magnification is usually set in the range of 5× to 5,000×. The focal length of the zone plate is preferably in the range of 1 millimeter (mm) to 100 mm.

In one version of the x-ray imaging systems of FIGS. 1 and 4, a sample container 110 is provided for containing the sample 103. Then the radiographs of the sample 103 are obtained while it is exposed to a controlled environment allowing fluid or gas flow experiments to be conducted during data acquisition so that one may perform live monitoring of the physical process in 3D. In another example, the sample is exposed to reactive fluids in the container and the radiographs obtained with the sample reacting with the fluids. In another example, a sample is exposed to a pressure gradient to test how the fluids flow through the sample.

Also, the x-ray imaging systems of FIGS. 1 and 4 are preferably mounted on a mobile platform inside a motorized vehicle 210 and with power supplied from the vehicle. This way, the quick turnaround mineral analysis is performed at the mining site.

While this invention has been particularly shown and described with references to preferred embodiments thereof, it will be understood by those skilled in the art that various changes in form and details may be made therein without departing from the scope of the invention encompassed by the appended claims.

What is claimed is:

1. A process of determining the porosity and/or internal composition inside a mineral sample with an x-ray imaging system, the process comprising:
   a. extracting core samples from different regions of the mineral sample;
   b. placing the core samples into an x-ray imaging system with magnification between 2× and 5,000×;
   c. acquiring magnified radiographs from x-rays transmitted through the core samples at different view angles; and
   d. reconstructing a 3D image of the core samples with computer tomography algorithms.

2. A process described in claim 1, wherein the core samples are shaped into cylindrical shapes with diameter of 10-1,000 micrometers.

3. A process described in claim 1, wherein the core samples are shaped into pillar shapes with width of 10-1,000 micrometers.

4. A process described in claim 1, wherein the core samples are shaped with mechanical grinding and polishing.

5. A process described in claim 1, wherein the core samples are shaped using lasers.

6. A process described in claim 1, wherein the x-ray imaging system comprises a laboratory-based x-ray source, a condenser lens, a sample holder with a rotation stage, an objective lens, and a spatially resolved detector system.

7. A process described in claim 6, wherein the x-ray source is a rotating anode x-ray source.

8. A process described in claim 6, wherein the x-ray source is a micro-focus x-ray source.

9. A process described in claim 6, wherein the condenser lens is an ellipsoid shaped capillary lens.

10. A process described in claim 6, wherein the objective lens is a Fresnel zone plate lens.

11. A process described in claim 6, wherein the detector comprises of a scintillator, a CCD camera, and a lens to image visible light image from the scintillator to the CCD camera.

12. A process described in claim 6, where the x-ray imaging system is placed on a mobile platform mounted inside a motorized vehicle and with power supplied from the vehicle.

13. A process described in claim 6, where the x-ray imaging system operates in the absorption contrast mode that records magnified x-ray shadow radiography.

14. A process described in claim 6, where the x-ray imaging system includes a phase-ring and operates in a phase contrast mode.

15. A process described in claim 6, where the sample is rotated through a range of −90 degrees and +90 degrees from the optical axis.

16. A process described in claim 15, where the rotation is performed in 0.25 to 1 degree steps.

17. A process described in claim 1, where x-ray imaging system generates x-rays with an energy of 5-150 keV.

18. A process described in claim 1, where the mineral sample is a rock sample such as sandstone, bituminous sand, ore sample, or coal.

19. A process described in claim 1, where the mineral sample includes precious metals.

20. A process described in claim 1, where the sample contains fluids, such as water or crude oil.

21. A process described in claim 1, wherein a mineral composition of the mineral sample is determined by measuring absorption properties of the core samples at different volumes.

22. A process described in claim 1, further comprising distinguishing metal clusters from other materials in the 3D computed tomography image.

23. A process described in claim 22, further comprising measuring a spatial distribution of the metal clusters using the 3D image.

24. A process described in claim 1, further comprising locating pores in the core samples from low-absorption regions in the 3D image.

25. A process described in claim 24, further comprising computing a porosity of the mineral sample by computing statistical properties of the pores.

26. A method of determining mineral composition of a mineral sample, the method comprising:
   acquiring magnified radiographs from x-rays transmitted through the mineral sample at different view angles;
   reconstructing a 3D image of the mineral sample with computer tomography algorithms;
   measuring absorption properties within different volumes of the 3D image; and
   determining a mineral content of the mineral sample from the absorption properties within the different volumes.

27. The method of claim 26, further including searching for precious metals by searching for volumes with a higher attenuation.

28. A method of determining porosity of a sample from an oil exploration and extraction operation, the method comprising:
   acquiring magnified radiographs from x-rays transmitted through a sample at different view angles;
   reconstructing a 3D image of the sample with computer tomography algorithms;
   identifying porous structures in the sample by measuring absorption characteristics or phase contrast; determining spatial distribution of the porous structures; and
   determining a porosity from the spatial distribution.

29. The method of claim 28, wherein the sample is identified as sandstone, bituminous sand, ore sample, coal, water, or oil based on the porosity of said sample.

* * * * *